(12) United States Patent
Taki et al.

(10) Patent No.: US 10,048,373 B2
(45) Date of Patent: Aug. 14, 2018

(54) OBJECT INFORMATION ACQUISITION APPARATUS OBJECT INFORMATION ACQUISITION METHOD AND NON-TRANSITORY COMPUTER-READABLE MEDIUM

(71) Applicant: CANON KABUSHIKI KAISHA, Tokyo (JP)

(72) Inventors: Hirofumi Taki, Kyoto (JP); Kenichi Nagae, Yokohama (JP); Toru Sato, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 27 days.

(21) Appl. No.: 15/586,156

(22) Filed: May 3, 2017

(65) Prior Publication Data

US 2017/0234982 A1 Aug. 17, 2017

Related U.S. Application Data

(63) Continuation of application No. 14/253,707, filed on Apr. 15, 2014, now Pat. No. 9,709,675.

(30) Foreign Application Priority Data

Apr. 18, 2013 (JP) .................. 2013-087828
May 20, 2013 (JP) .................. 2013-106485

(51) Int. Cl.
 *G01S 15/00* (2006.01)
 *G01S 15/89* (2006.01)
 (Continued)

(52) U.S. Cl.
 CPC ............ *G01S 15/8977* (2013.01); *A61B 8/14* (2013.01); *A61B 8/4483* (2013.01); *A61B 8/461* (2013.01);
 (Continued)

(58) Field of Classification Search
None
See application file for complete search history.

(56) References Cited

U.S. PATENT DOCUMENTS 5,785,657 A * 7/1998 Breyer .................. A61B 5/027
 600/454
5,844,140 A * 12/1998 Seale ...................... A61B 8/08
 73/633

(Continued)

FOREIGN PATENT DOCUMENTS

JP H04-92651 A 3/1992
JP H06-225878 A 8/1994
JP 2013-052073 A 3/2013

OTHER PUBLICATIONS

Electronic Industries Association of Japan; Handbook of ultrasonic diagnostic equipments, Revised Edition; Jan. 20, 1997; p. 19, Corona Publishing Co., Ltd.; Tokyo, Japan.

*Primary Examiner* — Isam A Alsomiri
*Assistant Examiner* — Jonathan D Armstrong
(74) *Attorney, Agent, or Firm* — Canon U.S.A., Inc. IP Division

(57) ABSTRACT

An object information acquisition apparatus according to an embodiment of the present invention includes a plurality of transducer elements each configured to transmit an acoustic wave to an object, to receive reflected waves reflected from inside the object, and to convert the reflected waves into a time-series reception signal; and a processor configured to perform frequency domain interferometry combined with adaptive signal processing by using the reception signals output from the plurality of transducer elements and a reference signal so as to obtain acoustic characteristics at a plurality of positions located inside the object. The processor is configured to switch the reference signal to another reference signal at least once in accordance with a target (Continued)

position located inside the object while performing the frequency domain interferometry so as to obtain the acoustic characteristics at the plurality of positions located inside the object.

20 Claims, 8 Drawing Sheets

(51) Int. Cl.
    *A61B 8/14*         (2006.01)
    *A61B 8/00*         (2006.01)
    *A61B 8/08*         (2006.01)

(52) U.S. Cl.
    CPC ........ *A61B 8/5207* (2013.01); *G01S 15/8918* (2013.01)

(56) References Cited

U.S. PATENT DOCUMENTS

| | | | |
|---|---|---|---|
| 6,381,197 B1* | 4/2002 | Savord | B06B 1/0292 367/178 |
| 6,685,645 B1* | 2/2004 | McLaughlin | A61B 8/08 600/447 |
| 7,999,945 B2* | 8/2011 | Zara | A61B 5/0066 356/479 |
| 8,214,010 B2* | 7/2012 | Courtney | A61B 5/0062 600/109 |
| 8,460,195 B2* | 6/2013 | Courtney | A61B 5/0062 600/459 |
| 9,304,191 B2* | 4/2016 | Nagae | G01S 15/8977 |
| 9,585,629 B2* | 3/2017 | Nagae | A61B 8/085 |
| 2007/0193354 A1* | 8/2007 | Felix | B06B 1/0292 73/514.32 |

\* cited by examiner

OBJECT INFORMATION ACQUISITION APPARATUS OBJECT INFORMATION ACQUISITION METHOD AND NON-TRANSITORY COMPUTER-READABLE MEDIUM

This application is a Continuation of U.S. patent application Ser. No. 14/253,707 filed Apr. 15, 2014, (now U.S. Pat. No.9,709,675), which claims the benefit of Japanese Patent Application No. 2013-087828 filed Apr. 18, 2013 and Japanese Patent Application No. 2013-106485 filed May 20, 2013. U.S. patent application Ser. No. 14/253,707, Japanese Patent Application No. 2013-087828, and Japanese Patent Application No. 2013-106485 are hereby incorporated by reference herein in their entirety.

BACKGROUND OF THE INVENTION

Field of the Invention

The present invention relates to an object information acquisition apparatus, an object information acquisition method, and a non-transitory computer-readable medium. More specifically, the present invention relates to a technique of acquiring object information by transmitting an acoustic wave to an object and receiving a reflected wave reflected from inside the object.

Description of the Related Art

In the case where image data is acquired by ultrasonic diagnostic apparatuses (i.e., object information acquisition apparatuses) using a pulse-echo method, the depth-direction spatial resolution can be generally expressed as $(n\lambda)/2$, where $\lambda$ denotes the wavelength of an ultrasonic wave and n denotes the number of transmitted waves. For example, in the case where two ultrasonic waves each having a center frequency of 12 MHz are transmitted, the depth-direction spatial resolution is approximately 0.13 mm.

The pulse-echo method will be described. First, an ultrasonic wave pulse (acoustic wave pulse) is transmitted to an object. The ultrasonic wave pulse is then reflected because of a difference in acoustic impedance inside the object, and a reflected wave returns. The reflected wave is received, and image data is generated using the reception signal of the reflected wave. Typically, the envelope of the reception signal is obtained, and the obtained envelope is converted into brightness values. In this way, image data is generated. By repeatedly performing transmission and reception of an ultrasonic wave in a plurality of directions or to a plurality of positions inside the object, pieces of brightness information can be acquired for a plurality of scan lines along the directions in which the ultrasonic wave is transmitted and received. The pieces of brightness information for the plurality of scan lines are then arranged. In this way, the inside of the object can be visualized.

In general, ultrasonic diagnostic apparatuses use a plurality of transducer elements each configured to perform conversion between an ultrasonic wave and an electric signal, and shift waveforms of signals of the individual transducer elements with respect to time. In this way, focusing is achieved inside the object during transmission and reception.

As described above, the pulse-echo method can achieve a depth-direction spatial resolution of approximately 0.13 mm. However, a higher spatial resolution is desired. For example, if more detailed observation of the layered structure of the blood vessel wall of the carotid artery becomes available, such observation may contribute to early detection of atherosclerosis or the like.

Hirofumi Taki, Kousuke Taki, Takuya Sakamoto, Makoto Yamakawa, Tsuyoshi Shiina, and Toru Sato, Conf Proc IEEE Eng Med Biol Soc. 2010; 1: 5298-5301 discloses a result obtained by imaging of the layered structure of the blood vessel wall by performing frequency domain interferometry (hereinafter, referred to as FDI method) and the Capon method which is a type of adaptive signal processing. By performing the FDI method and the Capon method for reception signals, the depth-direction (i.e., scan-line-direction) spatial resolution can be further improved. However, it is considered that a plurality of reflective layers may exist within a depth-direction range (i.e., processing range) of the signal sectioned for FDI processing. Also, it is likely that a plurality of reflected waves reflected from reflective layers located close to one another have a high correlation. It is known that if adaptive signal processing, such as the Capon method, is applied to such reception signals of the plurality of reflected waves having a high correlation without taking any additional measures, unexpected effects such as cancellation of a desired signal occur. In order to reduce the influence of signals having such a correlation (i.e., correlated interference waves), a frequency averaging technique is additionally used. In this way, the FDI method and the Capon method can be applied to reception signals of reflected waves.

In the case of using a frequency averaging technique for reception signals of acoustic waves having a wide frequency band, such as pulse waves, whitening is performed on the reception signals using a reference signal. Japanese Patent Laid-Open No. 2010-183979 discloses an apparatus that combines a plurality of criterion signals for forming a reference signal together at a predetermined interpolation ratio and uses the resulting signal (i.e., computation reference signal) as the reference signal.

As described above, adaptive signal processing in which the FDI method is employed (hereinafter, referred to as FDI-employed adaptive signal processing) uses a reference signal. As the waveform of this reference signal becomes closer to that of an actually obtained reflected wave, a higher spatial resolution is achieved by the FDI-employed adaptive signal processing.

However, the waveform of an acoustic wave pulse transmitted to an object changes depending on a position (i.e., reflection position) which the acoustic wave pulse reaches. In particular, the waveform of the transmitted acoustic wave pulse may change at positions of different depths. For this reason, there may be cases where a sufficiently high spatial resolution is not achieved by the FDI-employed adaptive signal processing.

SUMMARY OF THE INVENTION

In view of the aforementioned drawback, embodiments of the present invention aim to suppress the influence of a decrease in spatial resolution depending on a position in the case where FDI-employed adaptive signal processing is performed.

An embodiment of the present invention provides an object information acquisition apparatus including a plurality of transducer elements each configured to transmit an acoustic wave to an object, to receive reflected waves reflected from inside the object, and to convert the reflected waves into a time-series reception signal; and a processor configured to perform frequency domain interferometry combined with adaptive signal processing by using the reception signals output from the plurality of transducer elements and a reference signal so as to obtain acoustic characteristics at a plurality of positions located inside the object, wherein the processor is configured to switch the reference signal to another reference signal at least once in accordance with a target position located inside the object while performing the frequency domain interferometry so as to obtain the acoustic characteristics at the plurality of positions located inside the object.

An embodiment of the present invention provides an object information acquisition method for obtaining acoustic characteristics at a plurality of positions located inside an object by using a plurality of time-series reception signals output from a plurality of transducer elements each configured to receive reflected waves reflected from inside the object, the object information acquisition method including performing frequency domain interferometry combined with adaptive signal processing, by using the plurality of reception signals output from the plurality of transducer elements and a reference signal; and switching the reference signal to another reference signal at least once in accordance with a target position located inside the object.

Further features of the present invention will become apparent from the following description of exemplary embodiments with reference to the attached drawings.

DESCRIPTION OF THE EMBODIMENTS

The inventors have focused on the fact that the waveform of a transmitted acoustic wave changes depending on a position inside an object in the case where reflected waves reflected from inside the object are received and FDI-employed adaptive signal processing is performed on the received reflected waves. The inventors have noticed that an image may deteriorate if a difference is caused between the waveforms of the reflected waves and the waveform of a reference signal because of the change in the waveform of the transmitted acoustic wave.

Figure 1:
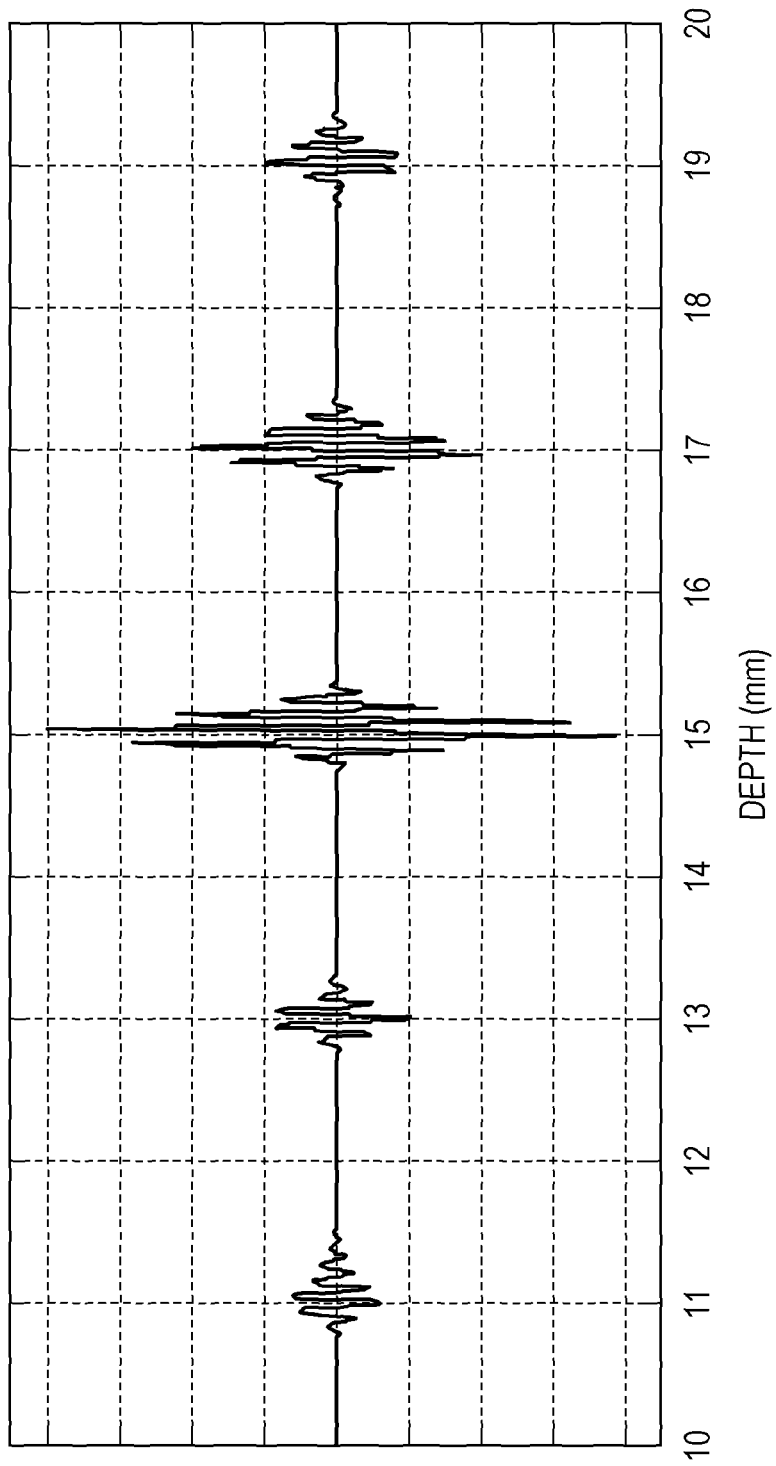
FIG. 1 is an explanatory diagram of a waveform of a reflected wave.

For example, a case will be described in which an acoustic wave is transmitted from a probe including one-dimensionally arranged transducer elements, such as capacitive micromachined ultrasonic transducers (CMUT) or piezoelectric transducers (PZT). FIG. 1 illustrates the waveform of an acoustic wave pulse at depths of 11 mm, 13 mm, 15 mm, 17 mm, and 19 mm in the case where the acoustic wave pulse is transmitted from a linear array of a plurality of one-dimensionally arranged transducer elements so that focusing is achieved at the depth of 15 mm. Herein, the term "depth" refers to a distance from the transducer elements. In this example, the transmission focus is set to the depth of 15 mm. Thus, the waveform at the depth of 15 mm is substantially the same as the transmitted waveform. However, as illustrated in FIG. 1, the waveforms at the other depths (of 11 mm, 13 mm, 17 mm, and 19 mm) are different from the transmitted waveform (i.e., waveform at the depth of 15 mm). In particular, the waveforms at shallow positions (located at small distances from the transducer elements) are largely different from the transmitted waveform.

Figure 2:
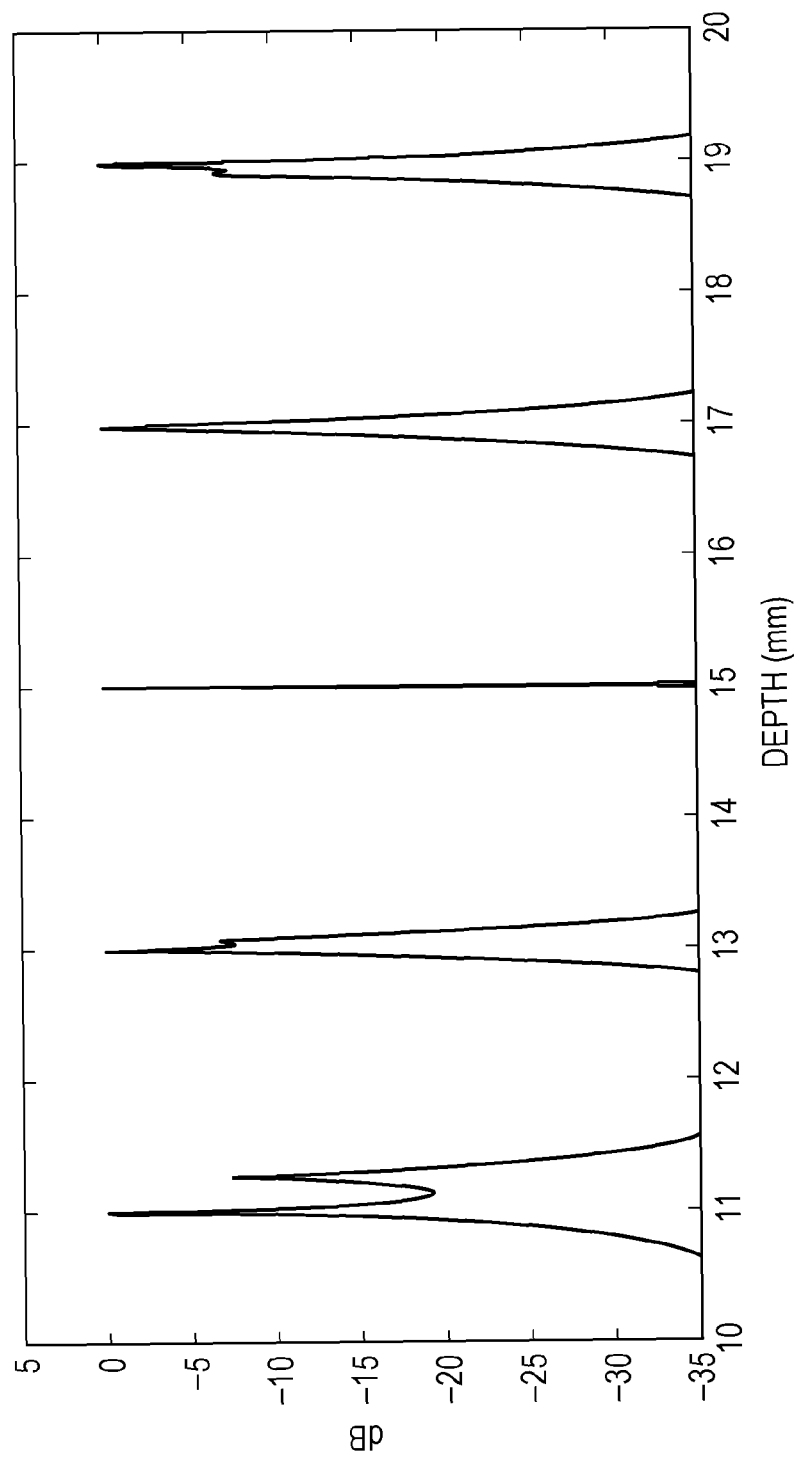
FIG. 2 is a diagram illustrating a power intensity of a reception signal having the waveform of the reflected wave illustrated in FIG. 1.

FIG. 2 illustrates a result obtained by performing FDI-employed adaptive signal processing by using the waveforms illustrated in FIG. 1 as reception signals and using the transmitted waveform (i.e., waveform substantially the same as the waveform at the depth of 15 mm) as a reference signal. It can be assumed that the waveform at each depth illustrated in FIG. 1 is substantially the same as the waveform of a reflected wave reflected from the depth. That is, it can be assumed that using each waveform illustrated in FIG. 1 as a reception signal is equivalent to receiving a reflected wave from a reflective plane existing at each of the depths (of 11 mm, 13 mm, 15 mm, 17 mm, and 19 mm).

The result illustrated in FIG. 2 confirms that a high resolution is achieved at the depth of 15 mm at which the waveform of the reception signal is substantially the same as that of the reference signal. In contrast, the power intensity of the processing result has two peaks at the depth of 11 mm and also has a wide half width for the peak. This implies that a sufficiently high spatial resolution is not achieved. Also, a spatial resolution as high as that achieved at the depth of 15 mm is not achieved at the depths of 13 mm, 17 mm, and 19 mm. Accordingly, in embodiments described below, the reference signal is switched to another one at least once in accordance with the depth inside an object while FDI-employed adaptive signal processing is being performed.

In embodiments of the present invention, the term "acoustic wave" typically refers to an ultrasonic wave, and includes an elastic wave called a sonic wave and an ultrasonic wave. An object information acquisition apparatus according to embodiments of the present invention includes an apparatus configured to transmit an acoustic wave to an object, receive reflected waves (i.e., reflected acoustic waves) reflected from inside the object, and acquire acoustic characteristics at a plurality of positions inside the object as values or image data. The acquired acoustic characteristics represent information reflecting a difference in acoustic impedance between tissues of the object. Also, in embodiments of the present invention, the term "scan line" refers to a virtual line formed in a direction in which an acoustic wave transmitted from a probe propagates.

Embodiments of the present invention will be described below with reference to the accompanying drawings. The same components are given the same reference numerals, and a description thereof is omitted.

Basic Configuration of Object Information Acquisition Apparatus

Figure 3:
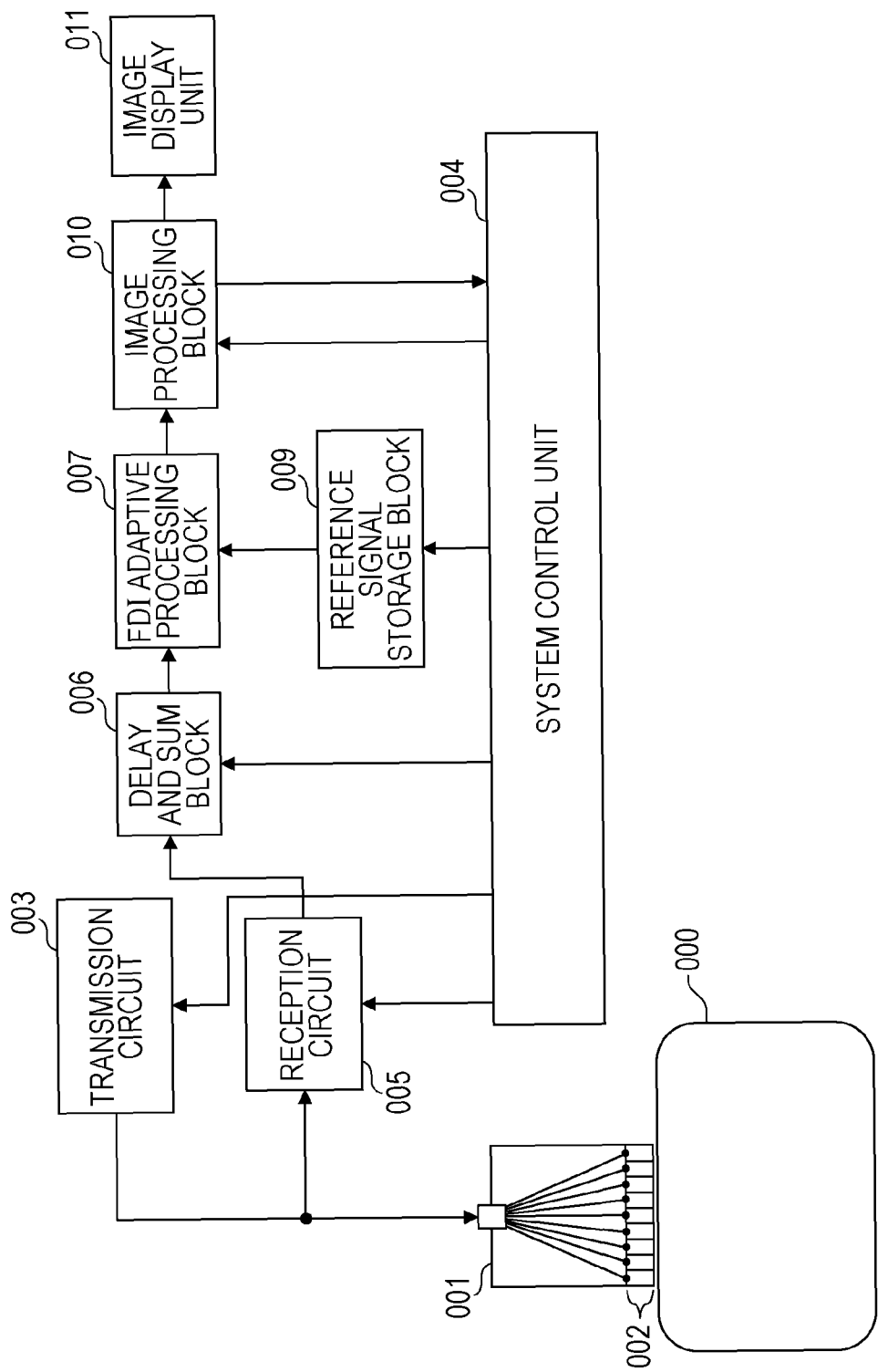
FIG. 3 is a schematic diagram illustrating an object information acquisition apparatus to which embodiments of the present invention is applicable.

FIG. 3 is a schematic diagram illustrating the configuration of an object information acquisition apparatus to which an embodiment of the present invention is applicable. The object information acquisition apparatus according to the embodiment includes a probe 001, a reception circuit 005, a transmission circuit 003, a delay and sum block 006, an FDI adaptive processing block 007, a reference signal storage block 009. The object information acquisition apparatus also includes an image processing block 010 and a system control unit 004. The probe 001 includes a plurality of transducer elements 002.

In the embodiment, the delay and sum block 006 corresponds to a delay and sum unit. The FDI adaptive processing block 007 corresponds to an FDI adaptive processing unit. The reference signal storage block 009 corresponds to a storage unit. The image processing block 010 corresponds to an image processing unit. Also, in the embodiment, at least the reception circuit 005, the transmission circuit 003, the delay and sum block 006, the FDI adaptive processing block 007, and the reference signal storage block 009 are included in a processor. Note that the processor may include the system control unit 004 and the image processing block 010 in the embodiment.

The probe 001 is a transceiver configured to transmit an acoustic wave to an object 000 and to receive reflected waves reflected from a plurality of positions inside the object 000. The probe 001 includes the plurality of transducer elements 002 each configured to perform conversion between an acoustic wave and an electric signal (i.e., a time-series reception signal). As the transducer elements 002, any given transducer elements capable of receiving an acoustic wave and converting the acoustic wave into an electric signal may be used. For example, transducer elements including piezoelectric elements based on the piezoelectric phenomena, transducer elements based on optical resonance, or transducer elements (such as CMUT) based on a change in static capacitance may be used. Preferably, the plurality of transducer elements 002 are arranged in an array shape, such as a one-dimensional or two-dimensional array.

The transmission circuit 003 generates a transmission signal (i.e., pulse signal) having a delay time and an amplitude according to a target position and a target direction, in accordance with a control signal supplied from the system control unit 004. The transmission signal is input to each of the plurality of transducer elements 002, and an acoustic wave is transmitted as a pulse wave to the object 000 from the plurality of transducer elements 002. The acoustic wave (i.e., reflected wave) reflected by a reflection interface or reflection body located inside the object 000 is received and converted into a plurality of reception signals by the plurality of transducer elements 002. The plurality of reception signals output from the plurality of transducer elements 002 are input to the reception circuit 005.

The reception circuit 005 is a circuit configured to amplify the time-series reception signals output from the transducer elements 002 and to convert the reception signals into a plurality of digital signals (i.e., digitized reception signals). The reception circuit 005 includes an amplifier and an analog-to-digital (A/D) converter. Note that, in the following description, a time-series reception signal output from one transducer element 002 which has received reflected waves in response to a single transmission of an acoustic wave pulse is treated as one reception signal. When there are M output channels, M reception signals corresponding to the M output channels are obtained in response to a single transmission of an acoustic wave pulse. Also, when one of transducer elements 002 transmits an acoustic wave pulse N times, N reception signals (i.e., N time-series reception signals) are obtained by the transducer element 002. Here, N and M denote positive integers. In addition, in embodiments of the present invention, the term "reception signal" refers to not only an analog reception signal output by the transducer element 002 but also a reception signal obtained by performing processing, such as amplification and A/D conversion. The plurality of digital signals output from the reception circuit 005 are input to the delay and sum block 006.

The delay and sum block 006 performs delay processing (phasing processing) on the plurality of digital signals in accordance with the direction in which or the position toward which the acoustic wave has been transmitted, and sums the resulting digital signals. That is, the delay and sum block 006 performs delay and sum processing. Then, a signal (scan line signal) having undergone the delay and sum processing is input to the FDI adaptive processing block 007. The term "scan line signal" refers to a signal along a propagation direction of beam-formed transmitted acoustic waves (i.e., an acoustic wave beam). In one scan line signal, intensities (intensity signals) of reflected waves reflected from a plurality of positions on the scan line are arranged in time series. A B-mode image displayed on general ultrasound apparatuses is obtained by arranging the envelopes of a plurality of scan line signals.

The FDI adaptive processing block 007 performs adaptive signal processing in which FDI processing is employed (hereinafter, referred to as "FDI adaptive processing") by using the plurality of scan line signals output from the delay and sum block 006 and a reference signal output from the reference signal storage block 009.

The adaptive signal processing corresponds to adaptive beam forming. Specifically, adaptive signal processing refers to processing for selectively extracting a reception signal of a desired wave arriving from the target direction or target position and suppressing reception signals of other unnecessary waves by adaptively changing processing parameters, such as a phase and a weight, in accordance with the reception signal. In particular, the Capon method which is a type of adaptive signal processing is a method in which processing is performed on a plurality of input signals so as to minimize outputs (power intensities) while keeping a sensitivity to the target direction or the target position fixed. The Capon method is also referred to as the directionally constrained minimization of power (DCMP) method or minimum variance method. Such adaptive signal processing beneficially improves the spatial resolution. In the embodiment, an example will be described in detail in which the Capon method is used as the adaptive signal processing. Although the Capon method is used in the embodiment, another type of adaptive signal processing (such as the multiple signal classification (MUSIC) technique or estimation of signal parameters via rotational invariant techniques (ESPRIT)) may be used.

The FDI method is a method for estimating a receive power at the target position by dividing a reception signal in terms of frequency and changing the phase of the divided signal in accordance with the target position. Note that the amount of change in phase can be determined in advance from a product of a distance from a certain reference position to the target position and the number of waves corresponding to the frequency.

That is, when the FDI method and the adaptive signal processing are used in combination, instead of using a predetermined weight and a predetermined amount of change in phase, a weight and an amount of change in phase which are calculated in accordance with the reception signal are used for the reception signal divided into frequency components so as to calculate the power intensity at the target position. Details about a process performed by the FDI adaptive processing block 007 will be described later with reference to FIG. 4. The power intensity calculated through the FDI adaptive processing in the embodiment corresponds to acoustic characteristics reflecting a difference in acoustic impedance between issues of the object. The image processing block 010 at the subsequent stage outputs a power intensity distribution constituted by a plurality of power intensities as image data.

The reference signal storage block 009 is a memory configured to store a plurality of reference signals having different waveforms for positions inside the object. Specifically, the reference signal storage block 009 stores a plurality of reference signals having different waveforms for positions in the depth direction of the object or transmission directions of the acoustic wave. Also, the reference signal storage block 009 may store a plurality of reference signals having different waveforms for combinations of the depth and the transmission direction. All the reference signals stored in the reference signal storage block 009 are not necessarily output from the reference signal storage block 009 as the plurality of reference signals.

The system control unit 004 instructs the reference signal storage block 009 to output two or more different reference signals while the FDI adaptive processing block 007 is performing the FDI adaptive processing. That is, the FDI adaptive processing block 007 switches the reference signal to another one at least once in accordance with the target position inside the object while performing the FDI adaptive processing. In particular, the FDI adaptive processing block 007 switches the reference signal to another one at least once in accordance with at least one of the depth (i.e., the time taken to receive the reflected wave) and the transmission direction of the acoustic wave.

In the case where the reference signal is switched to another one in accordance with the depth, the reference signal is switched at least once while the FDI adaptive processing is performed using one scan line signal. That is, the FDI adaptive processing is performed using different reference signals for an intensity signal corresponding to a first position on the one scan line signal and an intensity signal corresponding to a second position (different from the first position) on the same scan line signal. Note that the reference signal need not be switched to another one for each position. The reference signal is switched to another one at least once in accordance with the position while one scan line signal is processed, such that the FDI adaptive processing is performed using a first reference signal for shallow regions of the object and using a second reference signal for deep regions of the object. Also, the reference signals need not be prepared for respective positions and may be prepared for respective regions of a predetermined range. The plurality of power intensities acquired in this manner are output to the image processing block 010.

The image processing block 010 performs various kinds of image processing, such as smoothing and edge enhancement, on the power intensity distribution constituted by the plurality of input power intensities if necessary, and outputs brightness data (image data) to an image display unit 011. The image display unit 011 displays an image based on the input brightness data.

The FDI adaptive processing block 007 is constituted by a processing device, such as a central processing unit (CPU), a graphics processing unit (GPU), or a field programmable gate array (FPGA). Likewise, the system control unit 004 and the image processing block 010 are also constituted by a processing device, such as a CPU, a GPU, or an FPGA. The image display unit 011 is constituted by a liquid crystal display (LCD), a cathode ray tube (CRT) display, or an organic electroluminescence (EL) display. Note that the image display unit 011 may be provided separately from the object information acquisition apparatus according to the embodiment of the present invention.

Flow of FDI Adaptive Processing

Figure 4:
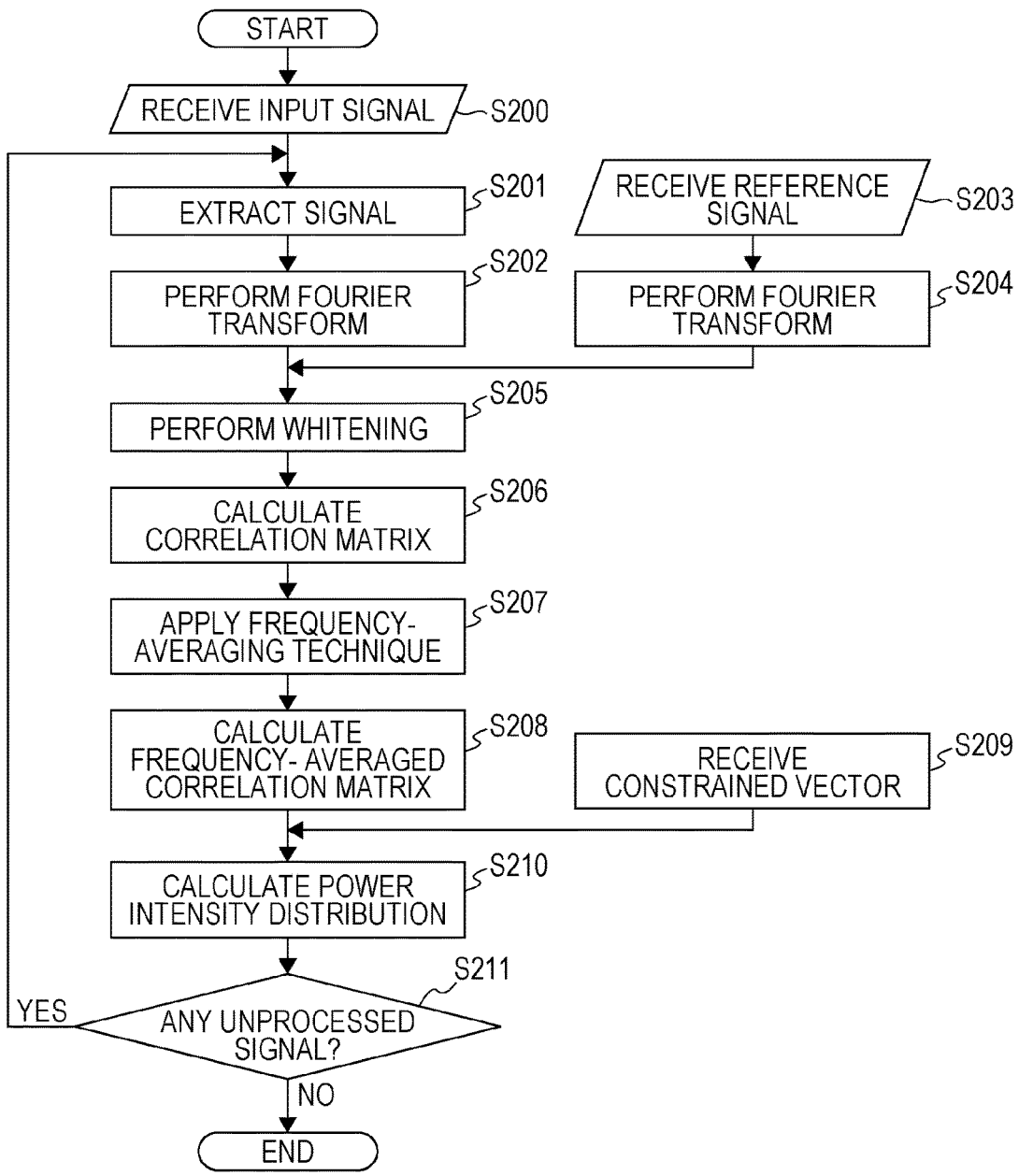
FIG. 4 is a flowchart explaining a process performed by an FDI adaptive processing block.

Referring now to FIG. 4, a process performed by the FDI adaptive processing block 007 will be described. FIG. 4 is a flowchart explaining each step of the FDI adaptive processing. The FDI adaptive processing block 007 receives, as an input signal, a scan line signal output from the delay and sum block 006 (S200). The FDI adaptive processing block 007 extracts an intensity signal for a period to be processed at a time (i.e., for a processing range) from the scan line signal (S201). At this time, the FDI adaptive processing block 007 may perform processing such as weighting of the intensity signal, in addition to extraction of the intensity signal for the processing range from a plurality of intensity signals of one scan line.

Then, the FDI adaptive processing block 007 performs Fourier transform on the extracted intensity signal so as to divide the extracted intensity signal into frequency components $X_{s1}, X_{s2}, X_{s3}, \ldots, X_{sN}$ (S202). Also, the FDI adaptive processing block 007 receives a reference signal that is output from the reference signal storage block 009 in accordance with an instruction from the system control unit 004 (S203).

The FDI adaptive processing block 007 then performs Fourier transform on the reference signal so as to divide the reference signal into frequency components $X_{r1}, X_{r2}, X_{r3}, \ldots, X_{rN}$ (S204). Note that, the reference signals may be stored in a form of frequency components to be used in the processing. In this case, Fourier transform can be omitted.

Then, the FDI adaptive processing block 007 performs whitening processing as expressed by Equation (1).

$$X_{wk} = \frac{X_{sk} X_{rk}^*}{|X_{rk}|^2 + \eta}, \tag{1}$$

where $X_{wk}$ (k=1, 2, ..., N) denotes frequency components obtained by the whitening processing, η denotes a constant term used for stabilization, and denotes a complex conjugate.

Subsequently, a correlation matrix R is calculated using a vector X including the frequency components obtained by the whitening processing (S206).

$$X = [X_{w1}, X_{w2}, \ldots, X_{wN}]^T \tag{2}$$

$$R = XX^{T*} \tag{3}$$

Here, T denotes a transpose. The correlation matrix R is a matrix having a size of N×N.

Then, sub-matrices are extracted from the correlation matrix R, and a frequency averaging technique is applied to the sub-matrices so as to average them (S207).

$$R' = \frac{1}{M} \sum_{m=1}^{M} R_m \tag{4}$$

$$R_{mij} = X_{w(i+m-1)} X_{w(j+m-1)}^* \tag{5}$$

Here, R' denotes a frequency-averaged correlation matrix and $R_m$ denotes a sub-matrix of the correlation matrix R having $R_{mij}$ as its elements.

In this way, the frequency-averaged correlation matrix R' is calculated (S208).

Here, M denotes the number of sub-matrices $R_m$ to be added together and each sub-matrix $R_m$ has a size of N+1−M. The number of sub-matrices $R_m$ to be added together, which is denoted by M, may be set such that M=N/2 is satisfied. Also, in the case where the correlation matrix R is created in accordance with a band of a reception signal of an ultrasonic wave, frequency components corresponding to a band located near the center have a high signal-to-noise (SN) ratio, that is, elements of the correlation matrix R located near the center have a high SN ratio. Accordingly, by setting the value M to have a relationship of M≥(N+1−M), the frequency-averaged correlation matrix R' including more elements of the correlation matrix R located near the center and having a high SN ratio can be created. When the value M is set in this manner, the frequency-averaged correlation matrix R' includes many elements having a high SN ratio. As a result, an improved resolution can be obtained more stably by the FDI adaptive processing.

Next, a constrained vector C is input to the FDI adaptive processing block 007 (S209). The constrained vector C is a vector that changes in accordance with a position r within the processing range and is defined by Equation (6) below.

$$C=[\exp(jk_1r), \exp(jk_2r), \ldots, \exp(jk_{(N-M+1)}r] \quad (6)$$

A power intensity distribution P(r) in the processing range is calculated using the frequency-averaged correlation matrix R' and the constrained vector C (S210).

$$P(r) = \frac{1}{C^{T*}(R' + \eta'E)^{-1}C}, \quad (7)$$

where η'E is added to stabilize calculation of an inverse matrix, and η denotes a constant or a value that changes depending on a value of $R_{xx,1}$, and E denotes a unit matrix.

If there is an unprocessed signal of the input signal (S211), the process returns to the extraction of the signal (S201) and is continued.

As described above, the FDI adaptive processing block 007 performs the FDI-employed adaptive signal processing by using, as its input signals, the plurality of scan line signals output from the delay and sum block 006 and the reference signals that are output from the reference signal storage block 009 in accordance with an instruction from the system control unit 004. Consequently, the FDI adaptive processing block 007 outputs a power intensity distribution.

Now, the reference signal which the system control unit 004 instructs the reference signal storage block 009 to output will be described. As described with reference to FIG. 1 or the like, the waveform of a transmitted pulse changes depending on the depth. As a result, a difference in waveform is caused between the reference signal and the reception signal, resulting in a low spatial resolution or a change in power value as illustrated in FIG. 2.

In the embodiment, how the waveform of a transmitted acoustic wave pulse changes is grasped in advance or is calculated in real time. The above-described FDI adaptive processing includes a step of switching the reference signal to another one at least once in accordance with the position inside the object. The reference signal is switched to another one at least once particularly in accordance with at least one of the depth (i.e., the time taken to receive the reflected wave) and the transmission direction of the acoustic wave. By switching the reference signal in this manner, processing can be performed in accordance with a change in the waveform that occurs at various positions inside the object. As a result, a high resolution can be stably achieved inside the object.

An object information acquisition apparatus according to another embodiment will be described in detail below with reference to the accompanying drawings. The same components are given the same reference numerals, and a description thereof is omitted.

First Embodiment

An object information acquisition apparatus according to a first embodiment has a configuration similar to that of the apparatus illustrated in FIG. 3. In the first embodiment, details about an instruction given to the reference signal storage block 009 from the system control unit 004 will be described in detail. The flow of a process other than this point is similar to that of the process described with reference to FIG. 4, and thus a description thereof will be omitted.

The reference signal storage block 009 according to the first embodiment stores a plurality of reference signals which are obtained in advance by performing calculation taking into consideration how a transmitted acoustic wave pulse changes depending on the depth. The system control unit 004 instructs the reference signal storage block 009 to change the reference signal to be output to the FDI adaptive processing block 007, in accordance with how the intensity signal contained in each scan line signal input to the FDI adaptive processing block 007 changes in accordance with the position or depth inside the object. Consequently, the FDI adaptive processing block 007 switches the reference signal to another one at least once in accordance with the target position in the depth direction of the object (i.e., the time taken to receive the reception signal) while performing the FDI adaptive processing.

Figure 5:
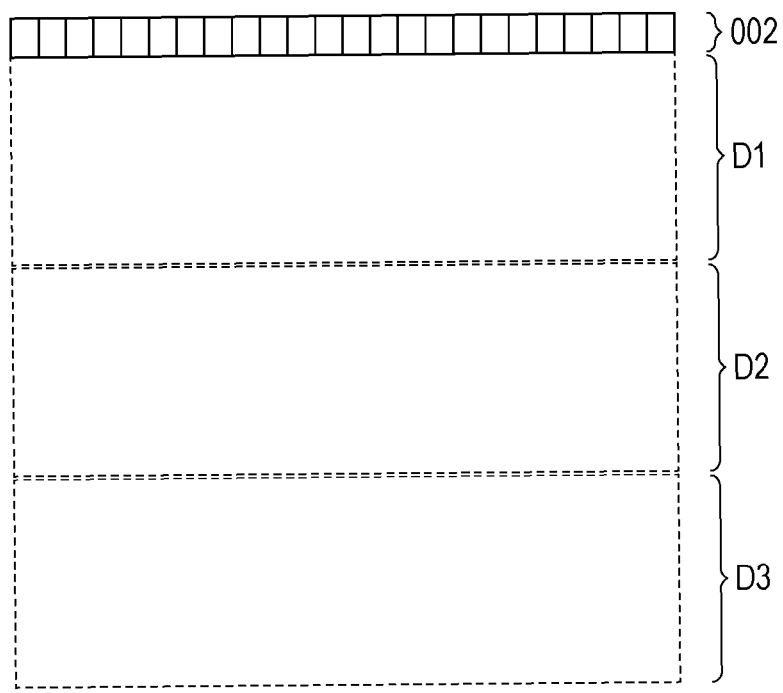
FIG. 5 is a schematic diagram illustrating an imaging region inside an object.

Referring to FIG. 5, how the system control unit 004 selects the reference signal will be described. FIG. 5 is a schematic diagram illustrating an imaging region (i.e., region for which a power intensity distribution is acquired) divided into a plurality of regions D1, D2, and D3 inside the object. Distances from the transducer elements 002 to the regions D1, D2, and D3 are different from one another. That is, the regions D1, D2, and D3 are located at different positions along the depth direction.

In the case of performing the FDI adaptive processing on intensity signals of reflected waves reflected from positions within the region D1, the system control unit 004 instructs the reference signal storage block 009 to output a reference signal calculated in consideration of a change in the waveform of the transmitted acoustic wave at a position within the region D1. In the case of performing the FDI adaptive processing on intensity signals of reflected waves reflected from positions within the region D2, the system control unit 004 instructs the reference signal storage block 009 to output a reference signal calculated in consideration of a change in the waveform of the transmitted acoustic wave at a position within the region D2. In the case of performing the FDI adaptive processing on intensity signals of reflected waves reflected from positions within the region D3, the system control unit 004 instructs the reference signal storage block 009 to output a reference signal calculated in consideration of a change in the waveform of the transmitted acoustic wave at a position within the region D3. Through this operation, the FDI adaptive processing can be performed using different reference signals for regions located at different distances in the depth direction.

Figure 6:
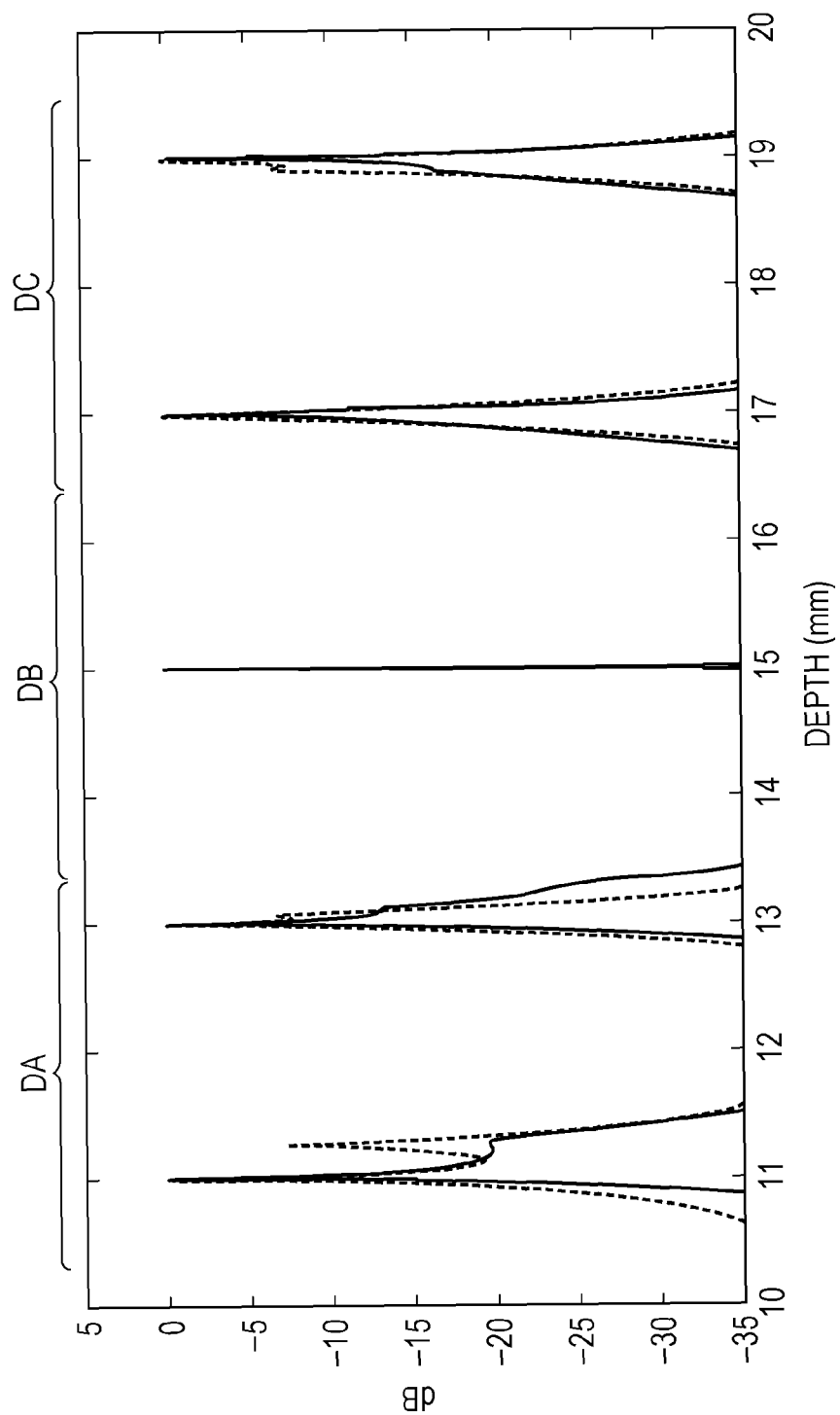
FIG. 6 is a diagram explaining benefits of a first embodiment.

Now, benefits of the first embodiment will be described. FIG. 6 is a diagram in which the power intensity distribution illustrated in FIG. 2 (denoted by a dotted line) and a power intensity distribution (denoted by a solid line) obtained by performing the processing according to the first embodiment are plotted. A region DA corresponds to the region D1, a region DB corresponds to the region D2, and a region DC corresponds to the region D3. The FDI adaptive processing is performed in the region DA using a reference signal calculated in consideration of a change in the waveform at the depth of 12 mm, in the region DB using a reference signal calculated in consideration of a change in the waveform at the depth of 15 mm, and in the region DC using a reference signal calculated in consideration of a change in the waveform at the depth of 18 mm. FIG. 6 reveals that the depth-direction spatial resolution of the power-intensity distribution according to the first embodiment is improved at each depth.

Figure 7:
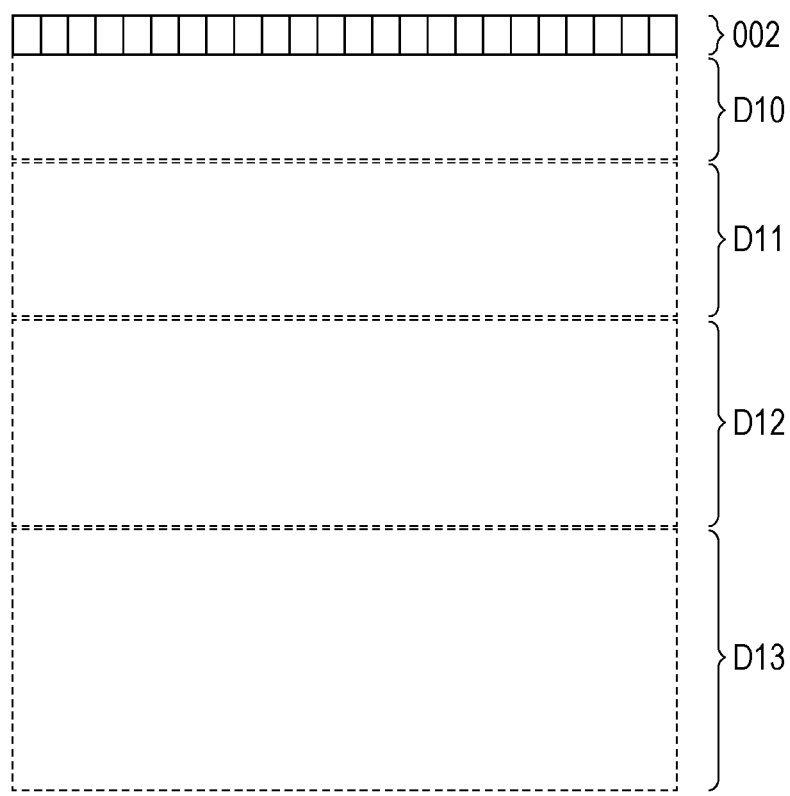
FIG. 7 is a schematic diagram illustrating an imaging region inside an object.

By using different reference signals for different regions inside the object, a high spatial resolution can be stably achieved. In the first embodiment, an example in which the imaging region is equally divided has been described. However, the imaging region may be divided into regions D10, D11, D12, and D13 as illustrated in FIG. 7. Specifically, in a part close to the transducer elements 002 (i.e., in a shallow region), the reference signal may be switched in units of narrower ranges. This is because a change in the waveform of a transmitted acoustic pulse is larger in a region closer to the transducer elements 002. By switching the to-be-used reference signal in units of narrow ranges in the region located closer to the transducer elements 002, a higher spatial resolution can be achieved.

In order to improve continuity at a boundary of the imaging regions, the imaging regions may be set to have an overlapping region. In this case, in the overlapping region, a new power intensity distribution is obtained by performing weighted addition on power intensity distributions calculated using different reference signals.

In the first embodiment, a single reference signal is used in a single region based on the assumption that reflected signals of the same waveform return from the region. However, even for the same region (typically, the same depth), the reflected waveform may possibly change depending on hardness or tilt of a reflective plane. In this case, the reference signal storage block 009 may prepare reference signals taking into consideration not only the position in the depth direction of the object but also hardness or tilt of the reflective plane. Specifically, in the processing flow, after the process ends as a result of selection of YES in S211 in FIG. 4 (i.e., after one image representing a power intensity distribution of the imaging region is obtained), the process returns to S203 and is repeated using reference signals different from the plurality of reference signals used in the previous processing flow. The reference signals used in the second process have different waveforms from the reference signals used in the first process in accordance with the hardness or tilt. Through this second process, another image representing a power intensity distribution of the same imaging region as that used in the first process is acquired. The image processing block 010 combines the images obtained through the first and second processes together, and outputs a combined image. With such a process, not only the case where the waveform of a transmitted wave changes depending on the depth but also the case where the reflected waveform changes depending on hardness or tilt of the reflective plane can be coped with.

Also, the first embodiment is applicable to the case of performing spatial compound imaging in which an acoustic wave pulse is transmitted toward a single position from a plurality of directions and acquired signals or images are superimposed or of performing multi-point focusing in which a plurality of transmission in-focus positions are set in the depth direction of the object and transmission is performed multiple times. That is, similar benefits are obtained by preparing reference signals in accordance with each transmission method in advance and performing the above-described FDI adaptive processing using the reference signals.

Second Embodiment

An object information acquisition apparatus according to a second embodiment has a configuration similar to that of the apparatus illustrated in FIG. 3. In the second embodiment, details about an instruction given to the reference signal storage block 009 from the system control unit 004 will be described in detail. The flow of a process other than this point is similar to that of the process described with reference to FIG. 4, and thus a description thereof will be omitted.

In the second embodiment, a sector scan is performed in which acoustic waves are transmitted at different angles using the transducer elements 002. In the case where acoustic wave pulses are transmitted from the plurality of transducer elements 002, the transmitted waveform may possibly change depending on the transmission angle (i.e., transmission direction). Accordingly, in the second embodiment, a plurality of reference signals having different waveforms are prepared in accordance with at least the transmission direction. That is, the reference signal is switched to another one at least once in accordance with the transmission direction. In the second embodiment, the transmitted waveform may possibly change depending on the depth as in the first embodiment. Accordingly, the following describes an example in which the reference signal is switched to another one in accordance with the distance from the transducer elements 002 (i.e., the depth) and the transmission direction of the acoustic wave.

In the second embodiment, the FDI adaptive processing block 007 performs the FDI adaptive processing using intensity signals corresponding to regions located at different distances from the transducer elements 002 (e.g., regions located at different depths just like regions 2C and 3C). At this time, the FDI adaptive processing block 007 uses reference signals having different waveforms depending on at least the depth. That is, the system control unit 004 instructs the reference signal storage block 009 to output different reference signals for the regions 2C and 3C.

Also, the FDI adaptive processing block 007 performs the FDI adaptive processing using intensity signals corresponding to regions, such as regions 3D and 3E, located at substantially the same distance from the transducer elements 002 but at different positions (i.e., transmission angles in this case). At this time, the FDI adaptive processing block 007 uses reference signals having different waveforms depending on at least the transmission direction. That is, the system control unit 004 instructs the reference signal storage block 009 to output different reference signals for the regions 3D and 3E.

Figure 8:
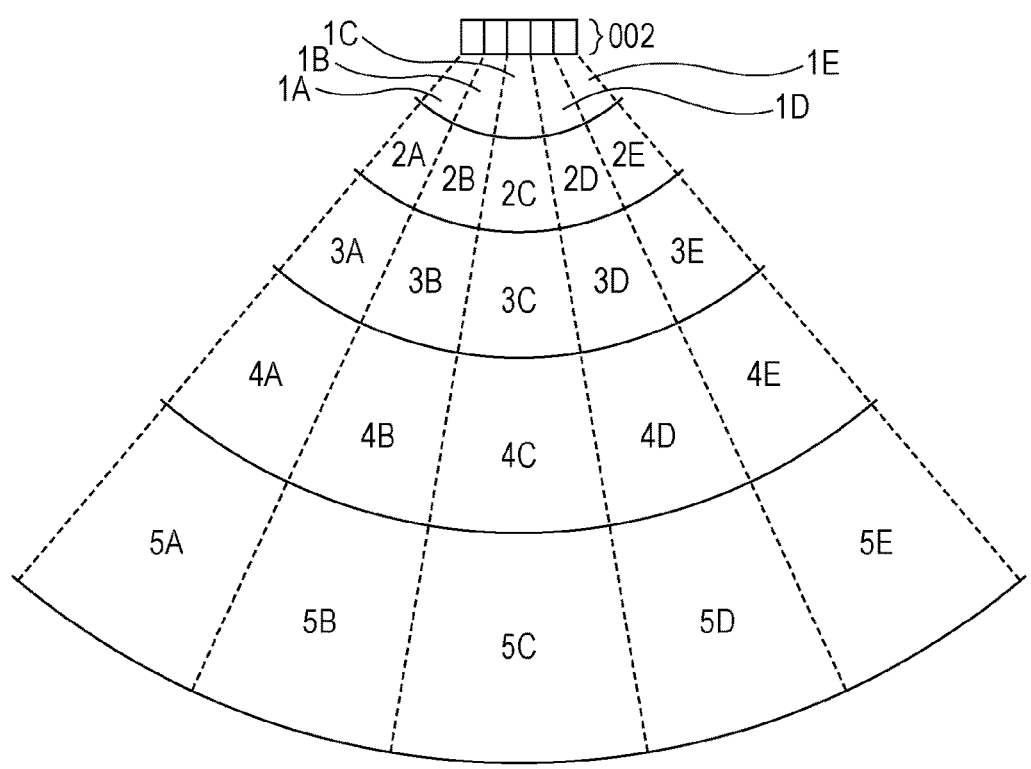
FIG. 8 is a schematic diagram illustrating an imaging region inside an object.

In the second embodiment, the same reference signal can be used for regions 4A and 4E or 5B and 5D which are located symmetrically. In such a case, similar benefits are obtained. The larger the transmission angle, the larger a change in the waveform of the transmitted acoustic wave. A "large transmission angle" refers to a direction in which tilt of the transmission direction with respect to the normal direction of the transducer elements 002 is large in FIG. 8. For example, the transmission angle is larger for the direction of a region 2E than for the direction of a region 2D. In the second embodiment, a higher spatial resolution can be achieved by switching the reference signal to another one in units of narrower angle ranges in a region of a large transmission angle than in a region of a small transmission angle.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to the embodiments of the present invention, in the case where FDI-employed adaptive signal processing is performed, the influence of a decrease in spatial resolution depending on a position can be suppressed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An object information acquisition apparatus comprising:
    a processor configured to perform frequency domain interferometry combined with adaptive signal processing by using reception signals output from a plurality of transducer elements in response to a reception of an acoustic wave transmitted from the plurality of transducers to an object and reflected by the object, and a reference signal so as to obtain acoustic characteristics at a plurality of positions located inside the object, wherein
    the processor is configured to apply different reference signals depending on a target position located inside the object while performing the frequency domain interferometry so as to obtain the acoustic characteristics at the plurality of positions inside the object, further wherein
    the processor is configured to apply different reference signals depending on hardness or tilt of a reflecting face inside the object.

2. The object information acquisition apparatus according to claim 1, wherein the processor performs for each of the plurality of reference signals, the frequency domain interferometry combined with adaptive signal processing.

3. The object information acquisition apparatus according to claim 2, wherein the processor combines the results of the frequency domain interferometry combined with adaptive signal processing using different reference signals.

4. The object information acquisition apparatus according to claim 1, wherein the processor changes the reference signals in terms of predetermined ranges when applying different reference signals depending on the target position.

5. The object information acquisition apparatus according to claim 4, wherein adjacent ones of the predetermined ranges have an overlapping region.

6. The object information acquisition apparatus according to claim 5, wherein the processor combines results of the frequency domain interferometry combined with adaptive signal processing of the overlapping region.

7. The object information acquisition apparatus according to claim 1, wherein the processor determines the predetermined ranges based on a time taken to receive each of the reflected waves.

8. The object information acquisition apparatus according to claim 1, wherein the processor determines the predetermined ranges based on at least one of depth and transmission direction of the acoustic wave.

9. The object information acquisition apparatus according to claim 1, wherein the processor performs as the adaptive signal processing, DCMP method, Capon method, MUSIC method, or ESPRIT method.

10. The object information acquisition apparatus according to claim 1, further comprising a memory configured to store the reference signals.

11. The object information acquisition apparatus according to claim 1, further comprising a probe having the plurality of transducers.

12. An object information acquisition method comprising:
    performing, using a processor, frequency domain interferometry combined with adaptive signal processing by using reception signals output from a plurality of transducer elements in response to a reception of an acoustic wave transmitted from the plurality of transducers to an object and reflected by the object, and a reference signal so as to obtain acoustic characteristics at a plurality of positions located inside the object, wherein
    different reference signals are applied depending on a target position located inside the object while performing the frequency domain interferometry so as to obtain the acoustic characteristics at the plurality of positions located inside the object, further wherein
    different reference signals depending on hardness or tilt of a reflecting face inside the object.

13. The object information acquisition method according to claim 12, further comprising:
    performing for each of the plurality of reference signals, the frequency domain interferometry combined with adaptive signal processing.

14. The object information acquisition method according to claim 13, further comprising:
    combining the results of the frequency domain interferometry combined with adaptive signal processing using different reference signals.

15. The object information acquisition method according to claim 12, further comprising:
    changing the reference signals in terms of predetermined ranges when applying different reference signals depending on the target position.

16. The object information acquisition method according to claim 15, wherein adjacent ones of the predetermined ranges have an overlapping region.

17. The object information acquisition method according to claim 16, further comprising:
   combining results of the frequency domain interferometry combined with adaptive signal processing of the overlapping region.

18. The object information acquisition method according to claim 12, further comprising:
   determining the predetermined ranges based on a time taken to receive each of the reflected waves.

19. The object information acquisition method according to claim 12, further comprising:
   determining the predetermined ranges based on at least one of depth and transmission direction of the acoustic wave.

20. The object information acquisition method according to claim 12, wherein DCMP method, Capon method, MUSIC method, or ESPRIT method is performed as the adaptive signal processing.

* * * * *